US011101039B2

(12) United States Patent
Albright

(10) Patent No.: US 11,101,039 B2
(45) Date of Patent: Aug. 24, 2021

(54) MACHINE-LEARNING-BASED FORECASTING OF THE PROGRESSION OF ALZHEIMER'S DISEASE

(71) Applicant: Jack Albright, Los Altos, CA (US)

(72) Inventor: Jack Albright, Los Altos, CA (US)

(*) Notice: Subject to any disclaimer, the term of this patent is extended or adjusted under 35 U.S.C. 154(b) by 163 days.

(21) Appl. No.: 16/290,896

(22) Filed: Mar. 2, 2019

(65) Prior Publication Data
US 2019/0272922 A1 Sep. 5, 2019

Related U.S. Application Data

(60) Provisional application No. 62/637,458, filed on Mar. 2, 2018.

(51) Int. Cl.
*G16H 50/20* (2018.01)
*G16H 50/50* (2018.01)
*G06N 3/04* (2006.01)
*G06K 9/62* (2006.01)
*G16H 50/70* (2018.01)

(52) U.S. Cl.
CPC ........... *G16H 50/20* (2018.01); *G06K 9/6267* (2013.01); *G06N 3/04* (2013.01); *G16H 50/50* (2018.01); *G16H 50/70* (2018.01)

(58) Field of Classification Search
CPC ......... G16H 50/20; G16H 50/50; G16H 50/70
USPC ....................................................... 705/2–3
See application file for complete search history.

(56) References Cited

U.S. PATENT DOCUMENTS

| 2012/0116795 A1* | 5/2012 | Ledley | G16H 10/40 |
| | | | 705/2 |
| 2015/0080703 A1* | 3/2015 | Reiman | A61B 5/4848 |
| | | | 600/409 |
| 2015/0247870 A1* | 9/2015 | Umlauf | G16H 50/20 |
| | | | 435/7.4 |

FOREIGN PATENT DOCUMENTS

WO WO2017106770 * 12/2016

OTHER PUBLICATIONS

Schmidt-Richberg et.al., "Learning Biomarker Models For Progression Estimation of Alzheimer's Disease", Plus One,(e0153040) 2016; 11(4): pp. 1-27. (Year: 2016).*
Aguilar, et.al., Different Multivariate Techniques For Automated Classification of MRI Data in Alzheimer's Disease and Mild Cognitive Impairment, Psychiatry Research: Neuroimaging, (2013), vol. 212: pp. 89-98 . (Year: 2013).*

(Continued)

*Primary Examiner* — Amber A Misiaszek
(74) *Attorney, Agent, or Firm* — Behmke Innovation Group; James M. Behmke; Jonathon P. Western

(57) ABSTRACT

According to one or more embodiments herein, a machine-learning algorithm is provided that uses current and past clinical data in order to accurately and precisely predict the future onset of mild cognitive impairment (MCI) and dementia for individual patients, thus enabling early identification of those having high risk for Alzheimer's disease. In particular, a newly defined "All-Pairs" technique combines data from each doctor's visit for each patient with data from each of the patient's other doctor's visits. By correlating clinical data obtained from patients at one time point with the progression of Alzheimer's disease in the future, the techniques herein are able to increase the likelihood of identifying Alzheimer's disease patients at early stages.

19 Claims, 13 Drawing Sheets

(56) References Cited

OTHER PUBLICATIONS

Iarlori, et.al., "RGBD Camera Monitoring System For Alzheimer's Disease Assessment Using Recurrent Neural Networks with Parametric Bias Action Recognition", The International Federation of Automatic Control Cape Town, South Africa, (2014): pp. 3863-3868. (Year: 2014).*
Zhang, et.al., "Predicting Future Clinical Changes of MCI Patients Using Longitudinal and Multimodal Biomarkers", (2012),Plus One ,, (e33182), vol. 7.: pp. 1-15. (Year: 2012).*
Maugh, Thomas, "Fight Against Alzheimer's Shows Results", Los Angeles Times, Los Angeles, CA, Nov. 1993, pp. 1-5 (Year: 1993).*
Recer, Paul, "Researchers discover link between gene, Alzheimer's", Bangor Daily News, Bangor, ME, Aug. 1993, pp. 1-3 (Year: 1993).*
ADNI General Procedures Manual, online: https://adni.loni.usc.edu/wp-content/uploads/2010/09/ADNI_GeneralProceduresManual.pdf, Sep. 2010, 120 pages, Alzheimer's Disease Neuroimaging Initiative.
Alzheimer's Disease Neuroimaging Initiative, Webpage: http://adni.loni.usc.edu/, 2017, 2 pages.
Cortez, Michelle, "Merck Will End Alzheimer's Trial as Alternative Approach Fails", Feb. 2018, 4 pages, Bloomberg News.
Cummings, et al., "Alzheimer's disease drug-development pipeline: few candidates, frequent failures", Jul. 2014, 7 pages, Alzheimer's Research and Therapy.
Gamberger, et al., "Identification of Clusters of Rapid and Slow Decliners Among Subjects at Risk for Alzheimer's Disease", Jul. 2017, 12 pages, Scientific Reports.
Hand, et al., "A Simple Generalisation of the Area Under the ROC Curve for Multiple Class Classification Problems", vol. 45, 2001, 16 pages, Machine Learning.
Humpel, Christian, "Identifying and validating biomarkers for Alzheimer's disease", Trends in Biotechnology, Jan. 2011, vol. 29, No. 1, pp. 26-32, doi: 10.1016/j.tibtech.2010.09.007.
Liu, et al., "Apolipoprotein E and Alzheimer Disease: Risk, Mechanismns, and Therapy", Feb. 2013, 27 pages, Nat Rev Neurol.
Mathotaarachchi, et al., "Identifying Incipient Dementia Individuals Using Machine Learning and Amyloid Imaging", Neurobiology of Aging, vol. 59, Nov. 2017, pp. 80-90, Elsevier.
Mu, et al., "Adult Hippocampal Neurogenesis and its Role in Alzheimer's Disease", Dec. 2011, 9 pages, Molecular Neurodegeneration.
Mumal, Iqra, "Poor Results Prompt Takeda and Zinfandel to End Phase 3 Alzheimer's Therapy Trial Early", alzheimersnewstoday.com/2018/01/31/takeda-and-zinfandel-bring-early-end-to-phase-3-trial-of-alzheimers-therapy-pioglitazone/, Jan. 2018, 2 pages.
Nestor, et al., "Ventricular Enlargement as a Possible Measure of Alzheimer's Disease Progression Validated Using the Alzheimer's Disease Neuroimaging Initiative Database", Sep. 2008, 12 pages, Brain.
Scikit-learn, Machine Learning in Python, webpage: https://scikit-learn.org/stable/, 2017, 2 pages.
Selkoe, et al., "Alzheimer's Disease is the Most Common Neurodegenerative Disorder", In: Siegel GJ, Agranoff BW, Albers RW, et al., editors. Basic Neurochemistry: Molecular, Cellular and Medical Aspects. 6th edition. Philadelphia: Lippincott-Raven; 1999. Available from: https://www.ncbi.nlm.nih.gov/books/NBK27944/.
Singanamalli, et al., "Cascaded Multi-view Canonical Correlation (CaMCCo) for Early Diagnosis of Alzheimer's Disease via Fusion of Clinical, Imaging and Omic Features", Aug. 2017, 14 pages, Scientific Reports.
Sperling, et al., "Toward defining the preclinical stages of Alzheimer's disease: Recommendations from the National Institute on AgingAlzheimer's Association workgroups on diagnostic guidelines for Alzheimer's disease", vol. 7, No. 3, May 2011, 24 pages, Alzheimers Dement.
"Functional Activities Questionnaire", online: https://www.healthcare.uiowa.edu/familymedicine/fpinfo/Docs/functional-activities-assessment-tool.pdf, 2006, 1page, Kaiser Permanente.
"Tadpole", online: https://tadpole.grand-challenge.org/, 7 pages, Jun. 2017, printed Dec. 2, 2019, EuroPOND Consortium and the Alzheimer's Disease Neuroimaging Initiative (ADNI).
"What we Know Today About Alzheimer's Disease", https://www.alz.org/research/science/alzheimers_disease_treatments.asp., Jul. 2010, 1 page, Alzheimer's Association.

* cited by examiner

Let $R$ be the number of patients. For each patient $P_i$ ($1 \leq i \leq R$), the ADNI database includes $L_i$ separate examinations by a physician. $E_{i,j}$, the $j$th examination of the $i$th patient, can be defined as follows:

$$E_{i,j} = [d_{i,j}, b_{i,j,1}, b_{i,j,2}, \ldots, b_{i,j,B}, C_{i,j}]$$

where $d_{i,j}$ is the date of the examination, $b_{i,j,k}$ ($1 \leq k \leq B$) are different biomarkers, and $c_{i,j}$ is the clinical state of the patient (NL, MCI, or dementia) as measured by that examination.

The All-Pairs technique uses this examination data to generate a feature array $X$ and target array $Y$. First, for every $i,j_a,j_b$, where $1 \leq i \leq R$ and $1 \leq j_a \leq j_b \leq L_i$, a row of $X$ and a corresponding cell of $Y$ is calculated:

$$X_{row} = [d_{i,j_b} - d_{i,j_a}, b_{i,j_a,1}, b_{i,j_a,2}, \ldots, b_{i,j_a,B}, C_{i,j_a}]$$
$$Y_{cell} = C_{i,j_b}$$

Second, the individual rows and cells are assembled to create the $X$ and $Y$ arrays. The $X$ array has $\sum_{i=1}^{R} \frac{L_i^2 - L_i}{2}$ rows and $B + 2$ columns, and the $Y$ array has $\sum_{i=1}^{R} \frac{L_i^2 - L_i}{2}$ rows and 1 column.

| TYPE OF BIOMARKER | BIOMARKER NAME | DESCRIPTION |
|---|---|---|
| Genetic | APOE4 | The APOE4 biomarker measures the number of copies (0, 1, or 2) of the ε4 allele of the gene encoding the enzyme Apolipoprotein E. This allele is the strongest genetic risk factor for Alzheimer's disease. |
| Physical | Hippocampus Ventricles/ICV | Physical measurements, like the volume of the hippocampus and the ventricles, can be used to assess the effect Alzheimer's disease has on the brain. |
| Behavioral | ADAS11 ADAS13 FAQ MMSE RAVLT (4 types) | Cognitive tests have been widely applied for early detection of Alzheimer's disease. |
| Demographic | Race Age | Demographic biomarkers can be used to account for general trends in a population. |

Table 400 - Features from the ADNI Dataset

FIG. 4

| VARIABLE 505 | MEANING 510 | 8-FEATURE TRAINING GROUP 515 | 11-FEATURE TRAINING GROUP 520 | 15-FEATURE TRAINING GROUP 525 |
|---|---|---|---|---|
| DX | Earlier Diagnosis | ✓ | ✓ | ✓ |
| ADAS13 | 13-item Alzheimer's Disease Assessment Scale | ✓ | ✓ | ✓ |
| Ventricles | Ventricular Volume | ✓ | ✓ | ✓ |
| AGE | Age | | ✓ | ✓ |
| FAQ | Functional Activities Questionnaire | | ✓ | ✓ |
| PTRACCAT | Race | ✓ | ✓ | ✓ |
| Hippocampus | Hippocampal Volume | ✓ | ✓ | ✓ |
| APOE4 | # of APOE4 Alleles | ✓ | | ✓ |
| MMSE | Mini-mental state examination | | ✓ | ✓ |
| ADAS11 | 11-item Alzheimer's Disease Assessment Scale | | ✓ | ✓ |
| RAVLT_immediate | Rey Auditory Verbal Learning Test - Total number of words memorized over 5 trials | | | ✓ |
| RAVLT_learning | Rey Auditory Verbal Learning Test - Number of words learned between trial 1 and trial 5 | | | ✓ |
| RAVLT_forgetting | Rey Auditory Verbal Learning Test - Number of words forgotten between trial 5 and trial 6 | | | ✓ |
| RAVLT_perc_forgetting | Rey Auditory Verbal Learning Test - Percentage of words forgotten between trial 5 and trial 6 | | | ✓ |
| N/A | Time Difference | ✓ | ✓ | ✓ |

Table 500 - Features from the ADNI Dataset Used to Train the MLP and RNN

FIG. 5

| Model*<br>605 | Train<br>mAUC<br>610 | Test | |
|---|---|---|---|
| | | mAUC<br>615 | Standard Deviation<br>617 |
| 8 Features, RNN, pairs | 0.939015 | 0.931809 | 0.014450 |
| 11 Features, RNN, pairs | 0.948332 | 0.935697 | 0.012182 |
| 15 Features, RNN, pairs | 0.950447 | 0.931987 | 0.014828 |
| 8 Features, MLP, pairs | 0.948956 | 0.941818 | 0.007267 |
| 11 Features, MLP, pairs | 0.954321 | 0.952339 | 0.008270 |
| 15 Features, MLP, pairs | 0.954957 | 0.951480 | 0.008254 |
| 8 Features, RNN, triplets | 0.964932 | 0.915778 | 0.011844 |
| 11 Features, RNN, triplets | 0.972427 | 0.923033 | 0.011844 |
| 15 Features, RNN, triplets | 0.969669 | 0.935656 | 0.023588 |
| 8 Features, MLP, triplets | 0.960821 | 0.963074 | 0.013336 |
| 11 Features, MLP, triplets | 0.966245 | 0.950462 | 0.012891 |
| 15 Features, MLP, triplets | 0.966912 | 0.948111 | 0.017367 |

*MLP = multilayer perceptron (e.g., implemented in *Scikit-learn*)

*RNN = recurrent neural network (e.g., implemented in *Keras/Tensorflow*)

Table 600 - Accuracy Metrics from Various Machine Learning Models (7-Fold Cross-Validation on 1737-Patient Training Dataset)

FIG. 6

|          | NL  | MCI | Dementia |
|----------|-----|-----|----------|
| NL       | 99% | 1%  | 0%       |
| MCI      | 37% | 53% | 9%       |
| Dementia | 12% | 38% | 50%      |

Predicted Diagnosis 905

Actual Diagnosis 910

900 - Confusion Matrix Comparing Predicted Diagnosis with Actual Diagnosis

FIG. 9

1000 - ROC Curves Based on Output of Neural Network

1100 - Month-by-Month Predicted Diagnosis for 110 Patients over 7 Years

MACHINE-LEARNING-BASED FORECASTING OF THE PROGRESSION OF ALZHEIMER'S DISEASE

RELATED APPLICATION

This application claims priority to U.S. Provisional Patent Application No. 62/637,458, filed Mar. 2, 2018, entitled MACHINE-LEARNING-BASED DETECTION OF ALZHEIMER'S DISEASE, by Jack Albright, the contents of which are hereby incorporated by reference in their entirety.

TECHNICAL FIELD

The present disclosure relates generally to the detection of diseases, and, more particularly, to machine-learning-based forecasting of the progression of Alzheimer's disease.

BACKGROUND

Alzheimer's disease is a type of dementia that causes problems with memory, thinking, and behavior, accounting for nearly 80% of dementia cases. Alzheimer's disease, in particular, is a chronic neurodegenerative disease that often starts slowly and worsens over time. For instance, the most common early symptom is difficulty in remembering recent events (short-term memory loss), while as the disease advances, symptoms can include problems with language, disorientation (including easily getting lost), mood swings, loss of motivation, behavioral issues, and so on. Eventually, the severity reaches the point where bodily functions are lost, ultimately leading to death (and is the sixth leading cause of death in the United States). Worldwide, Alzheimer's disease affects about 6% of people 65 years and older, and although the majority of people with Alzheimer's are 65 and older, cases of early-onset Alzheimer's (also known as younger-onset Alzheimer's) are also prevalent.

Unfortunately, the cause of Alzheimer's disease is not particularly well understood, typically believed to be genetic though possibly due to a history of injury or other illnesses. Furthermore, there is currently no known cure, and treatments only for symptoms are available (that is, not to stop Alzheimer's from progressing, but only to temporarily slow the worsening of dementia symptoms and to improve quality of life for those with Alzheimer's and their caregivers). Research on Alzheimer's disease continues, and there is a worldwide effort under way to find better ways to treat the disease, delay its onset, and prevent it from developing.

SUMMARY

According to one or more embodiments herein, a machine-learning algorithm is provided that uses current and past clinical data in order to accurately and precisely predict the future onset of mild cognitive impairment (MCI) and dementia for individual patients, thus enabling early identification of those having high risk for Alzheimer's disease. In particular, a newly defined "All-Pairs" technique combines data from each doctor's visit for each patient with data from each of the patient's other doctor's visits. By correlating clinical data obtained from patients at one time point with the progression of Alzheimer's disease in the future, the techniques herein are able to increase the likelihood of identifying Alzheimer's disease patients at early stages.

Other specific embodiments, extensions, or implementation details are also described below.

BRIEF DESCRIPTION OF THE DRAWINGS

The embodiments herein may be better understood by referring to the following description in conjunction with the accompanying drawings in which like reference numerals indicate identically or functionally similar elements, of which:

FIG. 2 illustrates an example mathematical model of a newly defined "All-Pairs" technique;

FIG. 3 illustrates an example graphical illustration of the All-Pairs technique;

FIG. 4 illustrates an example of features from an illustrative ADNI dataset;

FIG. 5 illustrates an example of features from the ADNI dataset used to train machine learning models (e.g., MLP and RNN);

FIG. 6 illustrates an example of accuracy metrics from various machine learning models;

FIG. 9 illustrates an example confusion matrix;

DESCRIPTION OF EXAMPLE EMBODIMENTS

Figure 1:
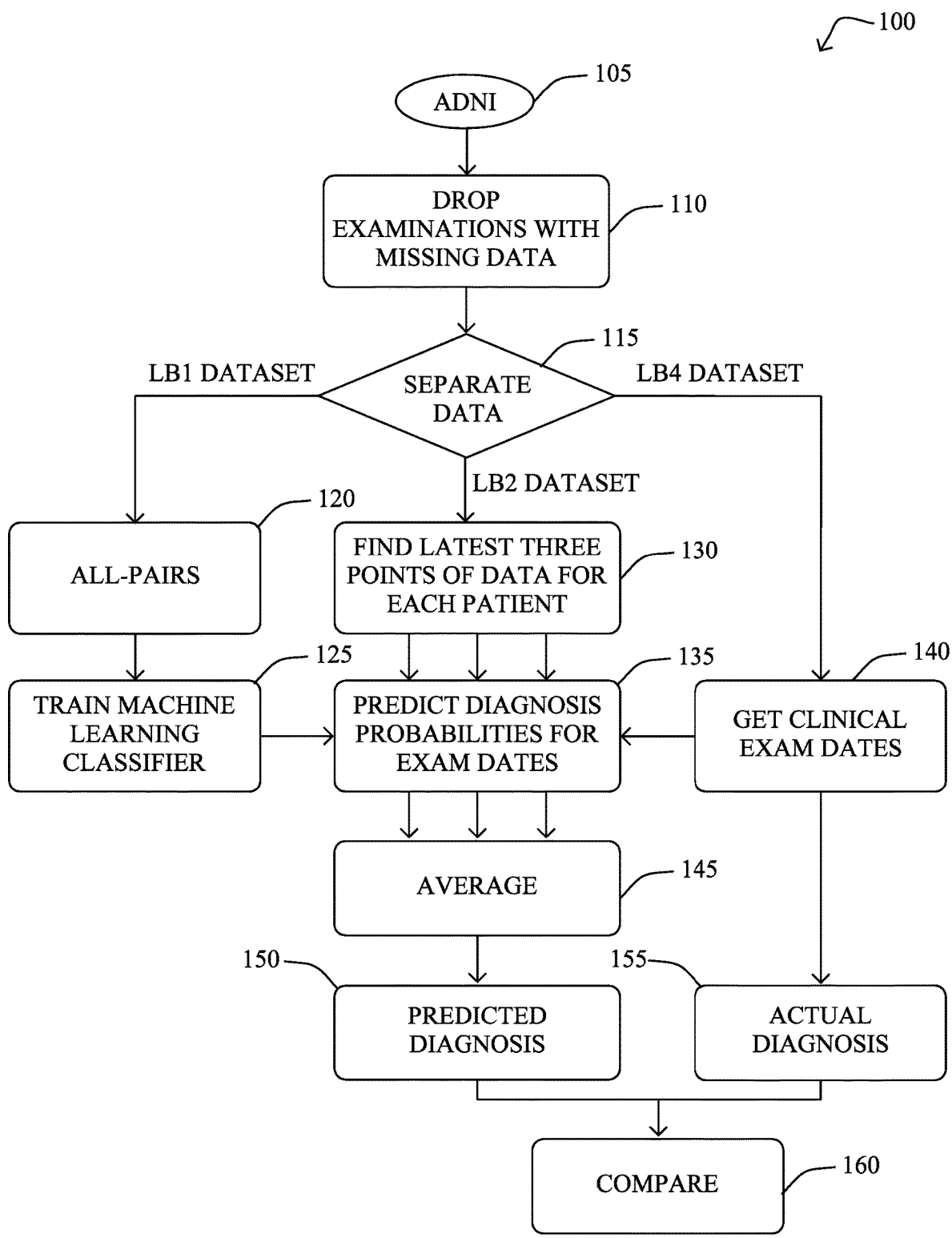
FIG. 1 illustrates an example flowchart for machine-learning-based forecasting of the progression of Alzheimer's disease.

As noted above, Alzheimer's disease is a chronic neurodegenerative disease that causes problems with memory, thinking, and behavior, where symptoms often start slowly and worsen over time. That is, as a progressive disease, dementia symptoms gradually worsen over a number of years. In its early stages, memory loss may be mild, but with late-stage Alzheimer's, individuals often lose the ability to carry on a conversation and respond to their environment.

In particular, the first "pre-dementia" symptoms of Alzheimer's disease are often mistakenly attributed to aging or stress, since mild cognitive difficulties can occur up to eight years before a person fulfils the clinical criteria for diagnosis of Alzheimer's disease. The most noticeable deficit is short term memory loss, which shows up as difficulty in remembering recently learned facts and inability to acquire new information. In this state, subtle problems with the executive functions of attentiveness, planning, flexibility, and abstract thinking, or impairments in semantic memory (memory of meanings, and concept relationships) can occur. Other neuropsychiatric symptoms, such as apathy, can be observed at this stage, and some may persist throughout the course of the disease. Depressive symptoms, irritability and reduced awareness of subtle memory difficulties are also common. The preclinical stage of the disease has also been termed "mild cognitive impairment" (MCI). This is often found to be a transitional stage between normal aging and dementia. MCI can present with a variety of symptoms, and when memory loss is the predominant symptom, it is termed "amnestic MCI" and is frequently seen as a prodromal stage of Alzheimer's disease.

In people with Alzheimer's disease, the increasing impairment of learning and memory eventually leads to a definitive diagnosis of dementia. In a small percentage, difficulties with language, executive functions, perception (agnosia), or execution of movements (apraxia) are more prominent than memory problems. Notably, Alzheimer's disease does not affect all memory capacities equally. For example, older memories of the person's life (episodic memory), facts learned (semantic memory), and implicit memory (the memory of the body on how to do things, such as using a fork to eat or how to drink from a glass) are often affected to a lesser degree than new facts or memories. Also, in early stage dementia, the person with Alzheimer's is usually capable of communicating basic ideas adequately, and certain coordination difficulties may be present, but generally unnoticed, unless they are cognitively demanding.

Progressive deterioration into a more moderate stage eventually hinders independence, where people become unable to perform most common daily activities, and begin to have more evident reading and writing problems and speech difficulties (e.g., inability to recall vocabulary). The risk of falling also increases, since complex motor sequences become less coordinated, and memory problems worsen, such as impairments to long-term memory (e.g., failing to recognize close relatives). In this stage, behavioral and neuropsychiatric changes can manifest into wandering, irritability, aggression, delusion, and so on.

During the advanced and final stages of Alzheimer's disease, the patient is completely dependent upon caregivers. Language is drastically reduced or eventually completely lost. Extreme apathy and exhaustion are common symptoms, and muscle mass and mobility deteriorate to the point where patients become completely dependent upon caregivers. Ultimately, the cause of death is usually an external factor, such as infection, pneumonia, etc., and not the disease itself.

Unfortunately, as also noted above, the cause of Alzheimer's disease is not particularly well understood, and there is currently no known cure. Research on Alzheimer's disease continues, for detection, prevention, treatment, and hopefully one day, a cure.

———Machine-Learning-Based Forecasting of the Progression of Alzheimer's———

As mentioned above, Alzheimer's disease is the most common neurodegenerative disease in older people. Alzheimer's disease takes a significant toll on patients' daily lives, causing a progressive decline in their cognitive abilities, including memory, language, behavior, and problem solving. Changes to Alzheimer's disease patients' cognitive abilities often start slowly and become more rapid over time. Doctors and other caregivers monitor the progression of Alzheimer's disease in patients by evaluating the degree of decline in the patients' cognitive abilities, which are often divided into three general categories: cognitively normal (NL), mild cognitive impairment (MCI), and dementia. Patients with MCI and dementia both suffer from reduced cognitive abilities, but MCI has a less severe effect on everyday activities, and patients suffering from dementia often have additional symptoms such as trouble with reasoning or impaired judgment.

Several different types of medical data (often referred to as "biomarkers") have been identified that are relevant to assessing the mental state of Alzheimer's disease patients and the progression of Alzheimer's disease in general. However, little-to-no progress has been made on developing a cure for Alzheimer's disease. For instance, though various medications have been approved by the Federal Drug Administration (FDA) to treat Alzheimer's disease, none have been shown to delay or halt its progression. Instead, they only temporarily improve patients' health. The most recently approved medication, for instance, is just the combination of two existing drugs for treating Alzheimer's disease, donepezil and memantine, which were approved by the FDA twenty-two and fifteen years ago, respectively.

Furthermore, despite considerable efforts to find a cure for Alzheimer's disease, there is still a 99.6% failure rate of clinical trials for Alzheimer's disease drugs. (Notably, in early 2018 alone, two groups ended their Alzheimer's disease clinical trials because their drugs failed to prevent the progression of Alzheimer's.) The difficulty in finding treatments for Alzheimer's disease is most likely a combination of uncertainty over the cause of Alzheimer's disease and the fact that Alzheimer's disease patients cannot easily be identified at early stages.

For this reason, Alzheimer's disease research would benefit from the ability to use current biomarkers to predict the mental state of patients in future years in order to identify patients who are good candidates for clinical trials before they become symptomatic. The techniques herein, therefore, provide a machine-learning algorithm that uses current and past clinical data in order to accurately and precisely predict the future onset of MCI and dementia for individual patients, thus enabling early identification of those having high risk for Alzheimer's disease, and who are therefore also good candidates for clinical trials for Alzheimer's disease therapeutics. That is, current and past clinical data from patients may be obtained (e.g., from the Alzheimer's Disease Neuroimaging Initiative (ADNI) database) and processed using a novel "All-Pairs" technique, which compares all possible pairs of temporal data points for each patient. This data can then be used to train various machine learning models. (Notably, the models were evaluated using 7-fold cross-validation on the training dataset and confirmed using data from a separate testing dataset—A neural network model was effective (mAUC=0.866) at predicting the progression of Alzheimer's disease on a month-by-month basis, both in patients who were initially cognitively normal and in patients suffering from mild cognitive impairment.) As noted, therefore, such a model could be used to identify patients at early stages of Alzheimer's disease and who may be good candidates for clinical trials, accordingly.

Operationally, the techniques herein use a variety of known biomarkers, which are measurable indicators (biological markers) of some state or condition. Though biomarkers for some biological states may be a certain substance whose detection indicates the presence of a condition, other biomarkers may take the form of other measurements and evaluations.

Several different types of biomarkers have been identified that are relevant to assessing the mental state of Alzheimer's disease patients and the progression of Alzheimer's disease in general, though others may be used or discovered over time. One of the largest genetic risk factors for Alzheimer's disease is the presence of 1 or 2 copies of the ε4 allele of the APOE gene, which encodes a particular variant of the enzyme Apolipoprotein E. Physical changes to the brain have also been shown to be correlated with the progression of Alzheimer's disease. For example, a decline in neurogenesis in the hippocampus (thought to be the center for emotion and memory inside the brain) is one of the earliest changes to brain physiology seen in Alzheimer's disease patients and is thought to underlie cognitive impairments associated with Alzheimer's disease. The progression of Alzheimer's disease also accelerates the normal atrophy of brain tissue caused by aging, as evidenced by increased enlargement of the ventricles of the brain over time. One study demonstrated a 4-fold difference in the rate of ventricle enlargement in Alzheimer's disease patients and normal controls over a six-month interval. The Ventricles/ICV (intracranial volume) is the ratio of the volume of the ventricles in a patient's brain to overall intracranial volume. Ventricles are cavities that produce cerebrospinal fluid. Volume measures are performed using MRI scans. In Alzheimer's disease, the ventricles of the brain are enlarged. Cognitive tests have also been widely used for early detection of Alzheimer's disease. Several commonly used tests, such as ADAS11 and ADAS13, are based on the Alzheimer's Disease Assessment Scale (ADAS), which is a brief cognitive test battery that assesses learning and memory, language production, language comprehension, constructional praxis, ideational praxis, and orientation (and is also referred to as the ADAS-Cognitive subscale or ADAS-Cog 11/13). ADAS11 scores range from 0 to 70, and ADAS13 scores range from 0 to 85, with higher scores indicating more advanced stages of Alzheimer's disease. Similar cognitive tests, such as the Mini-Mental State Examination (MMSE), the Rey Auditory Verbal Learning Test (RAVLT), and the Functional Activities Questionnaire (FAQ) have also been used to assess the progression of Alzheimer's disease in individual patients. ADAS has been found to be more precise than the MMSE (which consists of eleven different tasks that patients are asked to do, ranging from counting backwards from 100 by 7 s to making up a sentence about anything, and these tasks are graded to form an integer score out of 30, with 23 or below being signs of cognitive impairment), and the RAVLT only addresses verbal recall (e.g., the participant is given fifteen different words and is asked to repeat them back to the tester—this is done for the same set of fifteen words four times, then done with a new set of fifteen words, and then the participant has to repeat the original fifteen words), thus providing less diagnostic information than either of the other two. Similarly, the FAQ only assesses a patients' ability to perform certain tasks (such as writing checks or making a cup of coffee) and therefore is more limited in scope than the MMSE and ADAS.

In recent years, machine learning techniques have been applied to the diagnosis of Alzheimer's disease patients with great success. For example, using 3D convolutional neural networks to diagnose Alzheimer's disease achieved an accuracy of 94.1% on a dataset with 841 patients. Similar results were obtained by using a support vector machine to diagnose Alzheimer's disease based on an MRI scan dataset (n=427 patients; mean best accuracy=96.5%) and by using MRI scans, FDG-PET scans, and CSF biomarkers to diagnose Alzheimer's disease (n=202 patients; Alzheimer's disease vs. NL accuracy=93.2%, MCI vs. NL accuracy=76.4%). However, the focus of these earlier studies was to use current biomarkers to diagnose a patient's present cognitive state, in effect demonstrating that a computer can replicate a doctor's clinical decision-making. What is needed is a way to use machine learning to predict future diagnoses of Alzheimer's disease patients.

According to one or more embodiments of the techniques herein, and with reference generally to the example flowchart 100 in FIG. 1, the techniques herein may be configured to apply an "All-Pairs" technique, as described in detail below, to the preprocessed data (e.g., for regular time points, and excluding later time points, for all patients). In particular, as detailed below, under the All-Pairs technique, data from each doctor's visit for each patient is "paired" with data from each of the patient's other doctor's visits. Then from each pairing, the following data may be obtained:
i) a panel of clinical biomarkers from the earlier time point, including the diagnosis (normal, MCI, or dementia) at that time point;
ii) the time interval between the time points; and
iii) the diagnosis (normal, MCI, or dementia) at the later time point.

The All-Pairs technique, described in further detail below, may illustratively be implemented through various machine learning algorithms for classification problems, which may be trained with features (a list of observations or characteristics) and targets (the individual classifications that correspond to the features). In general, machine learning is concerned with the design and the development of techniques that take as input empirical data (such as the illustrative biomarkers listed above, among other features), and recognize complex patterns in these data.

As an example, one very common pattern among machine learning techniques is the use of an underlying model M, whose parameters are optimized for minimizing the cost function associated to M, given the input data. For instance, in the context of classification, the model M may be a straight line that separates the data into two classes (e.g., labels) such that $M=a*x+b*y+c$ and the cost function would be the number of misclassified points. The learning process then operates by adjusting the parameters a,b,c such that the number of misclassified points is minimal. After this optimization phase (or learning phase), the model M can be used very easily to classify new data points. Often, M is a statistical model, and the cost function is inversely proportional to the likelihood of M, given the input data. Notably, one class of machine learning techniques that is of particular use herein is clustering. Generally speaking, clustering is a family of techniques that seek to group data according to some typically predefined notion of similarity. For instance, clustering is a very popular technique used in recommender systems for grouping objects that are similar in terms of people's taste (e.g., because you watched X, you may be interested in Y, etc.). Other machine learning models, such as graph-based models (attempting to represent the relationships between different entities as a graph of nodes interconnected by edges), may also be used herein, and those mentioned herein are merely representative examples of machine learning algorithms.

For purposes of illustration of the techniques herein, the illustrative features can be represented by a matrix "X", while the targets can be represented by a matrix "Y". In order to generate X and Y for the ADNI time series data, data may be processed using a newly defined mathematical transformation, i.e., the "All-Pairs" technique, described below.

ADNI Data

Illustratively, data used in the preparation of the examples given herein were obtained from the Alzheimer's Disease Neuroimaging Initiative (ADNI) database (adni.loni.us-c.edu). The primary goal of ADNI has been to test whether serial magnetic resonance imaging (MRI), positron emission tomography (PET), other biological markers, and clinical and neuropsychological assessment can be combined to measure the progression of mild cognitive impairment (MCI) and early Alzheimer's disease (AD).

The ADNI study has been divided into several phases, including ADNI-1, ADNI-GO, and ADNI-2, which started in 2004, 2009, and 2011, respectively. ADNI-1 studied 800 patients, and each subsequent phase included a mixture of new patients and patients from the prior phase who elected to continue to participate in the study. The ADNI patient data was pre-processed to flag missing entries and to convert nonnumeric categories (such as race) into numeric data. Data was sorted into three datasets (LB1, LB2, and LB4) based on criteria established by The Alzheimer's Disease Prediction Of Longitudinal Evolution (TADPOLE) Challenge (https://tadpole.grand-challenge.org/). The LB2 and LB4 datasets consist of data from 110 patients who participated in ADNI-1, continued to participate in ADNI-GO/ADNI-2, and who were not diagnosed with Alzheimer's disease as of the last ADNI-1 time point. Specifically, LB2 contains all observations of these patients from ADNI-1, and LB4 contains all observations of these patients from ADNI-GO/ADNI-2. The LB1 dataset consists of ADNI data for all remaining patients (n=1737). Generally speaking, LB1 was used as a training and validation dataset, while LB2 and LB4 were later used to test the ability of machine learning models to predict the progression of AD on an independent patient population.

All-Pairs Technique

According to one or more of the embodiments herein, data (e.g., illustratively from LB1) may be further processed using a novel methodology referred to herein as the "All-Pairs" technique, which can be summarized as follows, and is described in illustration 200 of FIG. 2 using mathematical notation (and described below), and then illustrated in graphical form in example 300 of FIG. 3. Let R be the number of patients in the dataset and B be the number of biomarkers being evaluated as features. For each patient $P_i$ ($1 \leq i \leq R$), the ADNI database includes $L_i$ separate examinations by a physician. Then, $E_{i,j}$, the jth examination of the ith patient, can be defined as a multidimensional vector as follows:

$$E_{i,j} = [d_{i,j}, b_{i,j,1}, b_{i,j,2}, \ldots, b_{i,j,B}, c_{i,j}] \quad \text{Eq. 1}$$

where $d_{i,j}$ is the date of the examination, $b_{i,j,k}$ ($1 \leq k \leq B$) are different biomarkers, and $c_{i,j}$ is the clinical state of the patient (normal, MCI, or dementia) as measured during that examination. The All-Pairs technique transforms this examination data to generate a feature array X and target array Y that are used to train the machine learning models. Specifically, for every i, $j_a$, $j_b$, where $1 \leq i \leq R$ and $1 \leq j_a < j_b \leq L_i$, a row of X and a corresponding cell of Y are calculated:

$$X_{row} = [d_{i,j_b} - d_{i,j_a}, b_{i,j_a,1}, b_{i,j_a,2}, \ldots, b_{i,j_a,B}, c_{i,j_a}]$$

$$Y_{cell} = c_{i,j_b} \quad \text{Eq. 2}$$

This approach can be extended from pairs of examinations ($j_a, j_b$) to triplets ($j_a, j_b, j_c$) as follows:

$$X_{row} = [d_{i,j_c} - d_{i,j_b}, d_{i,j_b} - d_{i,j_a}, b_{i,j_b,1}, \ldots, b_{i,j_b,B}, c_{i,j_b}, b_{i,j_a,1}, \ldots, b_{i,j_a,B}, c_{i,j_a}] \quad \text{Eq. 3}$$

Individual rows and cells are then assembled to create the X and Y arrays that are used for training of the machine learning model as well as cross-validation studies. For pairs, the X array has B+2 columns, and the Y array has one column. Both the X array and Y array have a number of rows represented as:

$$\sum_{i=1}^{R} \frac{L_i^2 - L_i}{2} \quad \text{Eq. 4}$$

Figure 3:
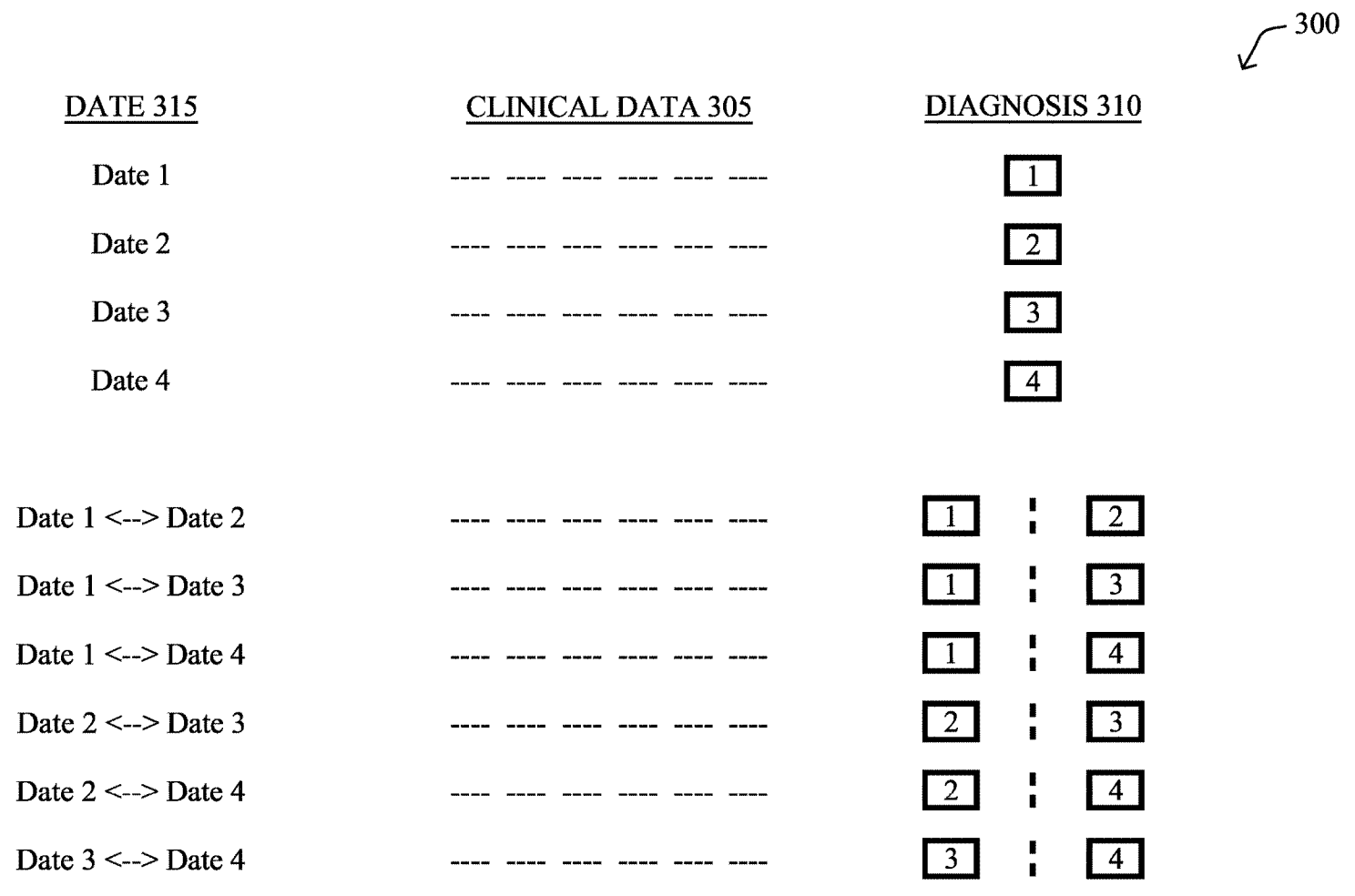

An example of this is represented graphically in FIG. 3.

In the case of LB2, each examination can be characterized by the same vector $E_{i,j}$ as used for the LB1 dataset. However, because the LB2 data is only used to test the machine learning models and not for training, no comparison between examinations is performed. Instead, $E_{i,j}$ is transformed into the input vector by replacing the $d_{i,j}$ term with a time variable that represents the number of months into the future that the machine learning model should make a prediction. Specifically, for each patient $P_i$ in LB2, the machine learning algorithm is applied to a series of input vectors of the form:

$$[t, b_{i,j,1}, b_{i,j,2}, \ldots, b_{i,j,B}, c_{i,j}] \quad \text{Eq. 5}$$

where t is the time variable. Input vectors are generated based on each patient's last three examinations in LB2, or for all of the examinations if the patient has less than three examinations. The probabilities calculated by the machine learning algorithm based on these examinations are averaged to generate predicted probabilities for patient $P_i$ at time t. When comparing the model's predictions against the actual diagnoses in LB4, t is set to the time difference between the applicable exam in LB2 and the applicable exam in LB4. For example, for the time course shown in FIG. 11, t is set to an integer between 1 and 84, inclusive.

FIG. 3 illustrates an example of pairing the clinical data 305 with the diagnosis 310 (e.g., 1-4) from different corresponding times 315 (e.g., 1-4). As can be seen, each diagnosis is paired with another diagnosis across a corresponding time difference, and used for the machine learning techniques herein, accordingly, as described herein.

Referring again to FIG. 1, flowchart 100 summarizes the overall methodology for training and evaluating machine learning models. In particular, ADNI data 105 is obtained, and examinations with missing data is dropped/filtered in 110. The remaining data may then be separated (115) into the LB1, LB2, and LB4 datasets. In 120 the illustrative and novel all-pairs technique pre-processes the LB1 data. From this pre-processed data, in 125 a machine learning classifier can be trained (e.g., and cross-validated). With the LB2 data, the latest three (or other value) points of data are found in 130, such that in step 135 the machine learning classifier (from 125) can be used on the corresponding points of data from 130 to predict diagnosis probabilities for exam dates in 135 (e.g., using clinical exam dates 140 from LB4 to calculate the appropriate time difference to use as input for the machine learning model). The predicted diagnosis probabilities can be averaged (145) to create a predicted diagnosis 150, which can then be compared to the actual diagnosis 155 in step 160 to determine the achieved accuracy (and to further correct the machine learning models).

Biomarkers

The features analyzed by the machine learning models consisted of a set of 13 biomarkers present in the ADNI data, all of which have been cited in published papers as correlating with Alzheimer's disease progression. These 13 biomarkers are summarized in Table 400 of FIG. 4 and include genetic markers (APOE4), physical measurements (ventricular volume/ICV ratio, hippocampal volume), the results of behavioral tests (ADAS13 and ADAS11 scores, FAQ score, MMSE score, and 4 types of RAVLT scores), and basic demographic information (age and race). As described above, two additional features that were generated during pre-processing of the data using the All-Pairs technique were also included in the models, namely, the clinical diagnosis at the earlier of two examinations and the time difference between examinations.

—Results—
Model Performance

Various machine-learning classifiers, including support vector machines, logistic regression, gradient boosting classifiers, random forests, multilayer perceptron neural networks, and recurrent neural networks, may be implemented, such as by using the Python libraries Scikit-learn and Keras (backed by TensorFlow). Each classifier may then be evaluated on the processed data derived from LB1 using 7-fold cross-validation.

The effectiveness of each classifier was measured using a specialized version of an ROC-AUC (Receiver Operating Characteristic Area Under the Curve) score for multiclass classification ("mAUC score"). The ROC-AUC score is a balanced metric for classifiers that considers both the true positive rate (percentage of actual positives that are called correctly) and the false positive rate (percentage of actual negatives that are called incorrectly). The mAUC variant of this score takes all ordered pairs of categories (i,j), measures the probability that a randomly selected element from category i would have a higher estimated chance of being classified as category i than a randomly selected element from category j, and averages all of these probabilities. A classifier that works perfectly would have an mAUC score of 1; a classifier that guessed randomly would result in an mAUC score of 0.5.

In the end, two classifiers, a multilayer perceptron implemented in Scikit-learn ("MLP") and a recurrent neural network implemented in Keras ("RNN") were found to have the best performance in the cross-validation studies. Both of these classifiers are types of neural networks. An MLP consists of a layer of input nodes, a layer of output nodes, and one or more hidden layers between the input and output layers. Each input vector is fed into the input nodes, and the value of each node in every other layer is dependent on the values of the nodes in the previous layer. Like an MLP, an RNN consists of multiple nodes organized into layers, but the outputs of some of the hidden layers are fed back into the same layer so that earlier input vectors can influence the outputs for later input vectors. This allows the RNN to "remember" earlier inputs, which has been shown to be particularly useful when analyzing data consisting of multiple observations taken at different time points.

To further investigate the MLP and the RNN and see if the performance of the MLP and RNN could be further improved by optimizing the training protocol, six variants of each of the neural networks were generated to examine the effects of changing the number of features (i.e., biomarkers plus time intervals) being examined (8, 11, and 15) and whether the All-Pairs technique was applied to pairs of patients' doctors' visits or triplets of visits. Table 2 of FIG. 5 details which features were included in the 8, 11, and 15-feature training groups. The columns in Table 500 labelled "Variable" 505 and "Meaning" 510 provide the name of each feature as it appears in the ADNI dataset as well as the corresponding description for each feature, respectively. (Notably, the remaining columns refer to 8-feature training group 515, 11-feature training group 520, and 15-feature training group 525, respectively.)

Table 600 of FIG. 6 shows the resulting mAUC scores after training (scores 610) and testing (scores 615) the 12 models 605 on LB1-derived data using 7-fold cross-validation, as well as the standard deviations 617 for the testing mAUC scores. The best performing model was the MLP trained on 8 features and triplets of time points, as it had the highest testing mAUC score. This model 608 is highlighted in FIG. 6. However, the differences among all of these models are quite small and in many cases well within 1 standard deviation (s.d.), suggesting that some of the variability between the scores might be due to random chance rather than actual differences in predictive performance. Additionally, because the training and testing of neural networks, as well as the cross-validation process, relies to some extent on algorithms that utilize random numbers, the scores in the table below will change slightly each time that the models are subjected to cross-validation.

Figure 7:
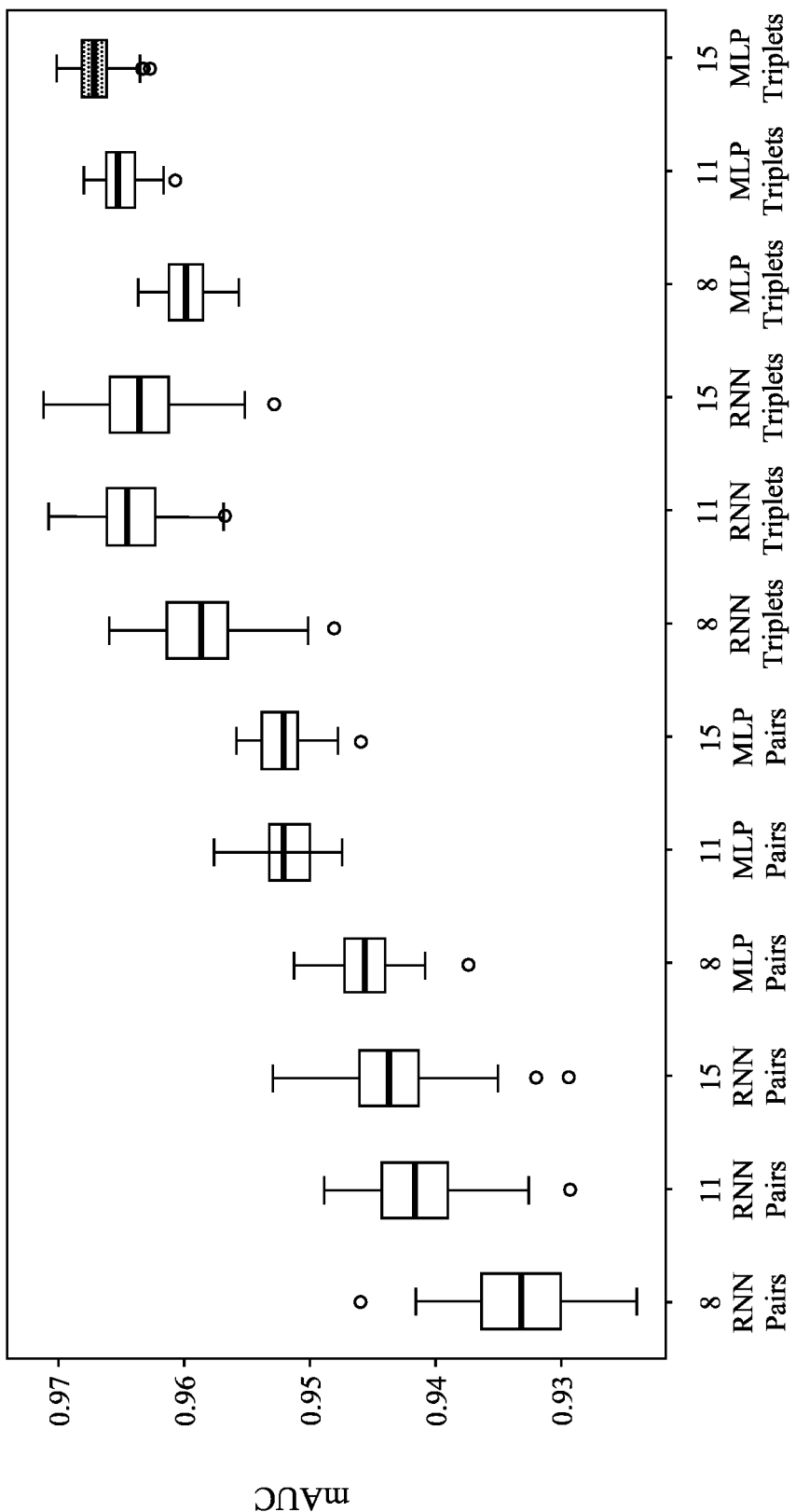
FIG. 7 illustrates an example of performance of various machine learning models.

In order to assess the performance of these models in a more rigorous manner, each of the 12 models was also evaluated on a series of random splits of the preprocessed LB1 dataset. For each model, the preprocessed LB1 dataset was randomly separated into a training dataset and testing dataset using a 70:30 ratio, and this was repeated to create 100 pairs of training and testing datasets that were then used to train and test the model. The use of a large number of randomly generated splits produces a distribution of mAUC scores that better reflects the overall performance of the model and minimizes the effects of outliers. The results are shown as box-and-whisker plots 700 in FIG. 7. Using this more rigorous approach, the model with the highest average mAUC score was an MLP trained on data with 15 features and with triplets of patients' examinations, which had an average mAUC score of 0.967 and a standard deviation of 0.0016. This model is highlighted as data point 705 in FIG. 7.

Prediction of Alzheimer's Disease Progression

In order to assess real-world performance, select models were also trained on the entire LB1 dataset (after processing with the All-Pairs technique) and then evaluated on data derived from LB2 and compared to actual diagnoses in LB4, asking whether early biomarkers for the 110 patients in LB2 can predict their later diagnoses. The actual examination dates in LB4 vary from patient to patient, but they generally cover the 7-year period of ADNI-GO/ADNI-2. LB4 contains a total of 417 examinations, or an average of 3.79 examinations per patient. As in the cross-validation studies, the performance of each model was assessed based on mAUC scores. Out of the 12 previously discussed models, the four models that used 15 features were selected for testing against LB2/LB4, namely:

1. MLP trained using pairs of examinations,
2. MLP trained using triplets of examinations,
3. RNN trained using pairs of examinations, and
4. RNN trained using triplets of examinations.

Figure 8:
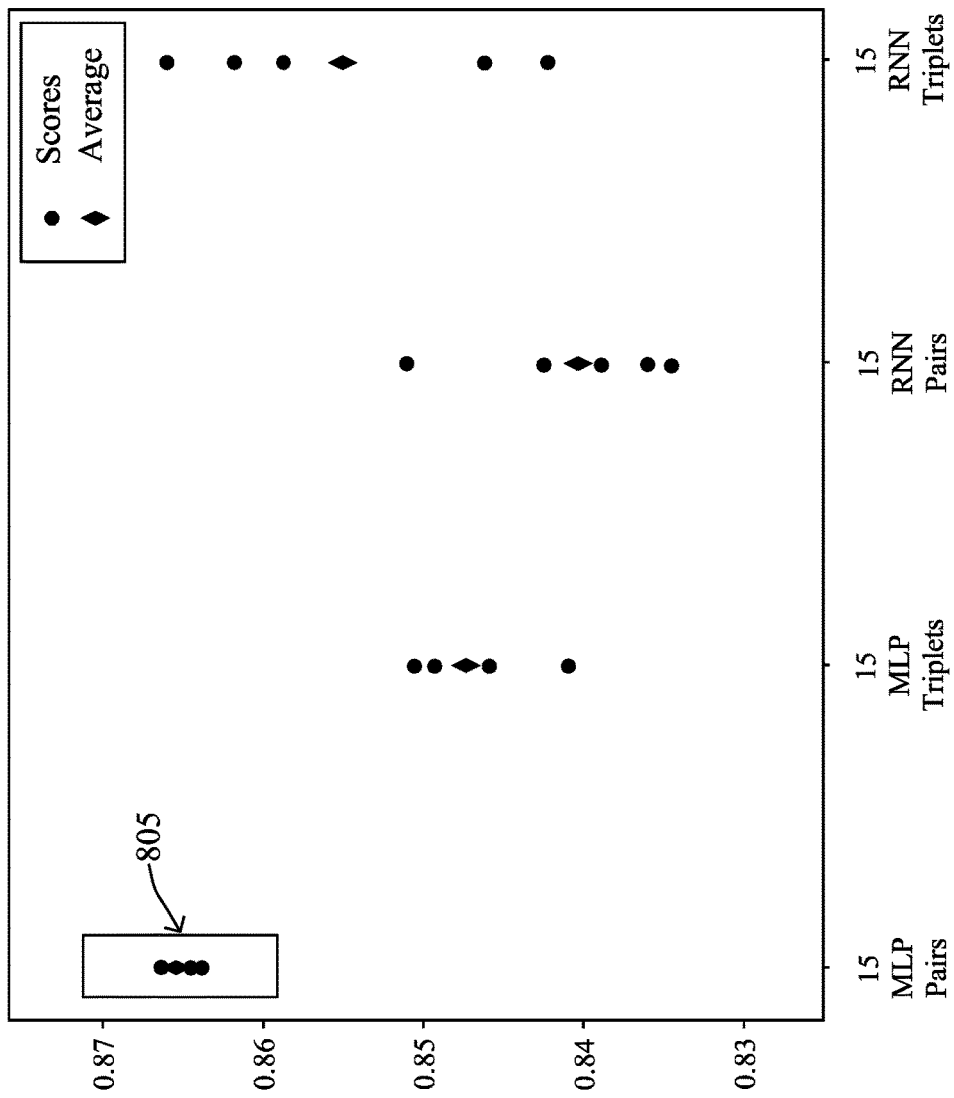
FIG. 8 illustrates another example of performance of various machine learning models.

Hyper-parameter optimization was conducted for each of these models, and each model was tested five times for each set of parameters to minimize the impact of random variation inherent in the neural network training process. In total, 27 different sets of parameters were tested for each model, consisting of three possible values for the alpha parameter, three possible values for the learning rate, and three possible values for the size of the hidden layers. FIG. 8 shows the results 800 from the highest performing version of each of the four models listed above.

The model and parameters with the best average mAUC score was the MLP trained on 15 features using pairs of examinations, which achieved an average score of 0.866 on the 110-patient test dataset. This model is shown with box 805 in FIG. 8. These results represent an improvement over previously published work using the ADNI dataset. (In particular, a random forest classifier technique achieved an mAUC score of 0.82; an RNN achieved an mAUC score of 0.7596; and an RNN together with forward-filling data imputation achieved an average mAUC score of 0.86.)

FIG. 9 depicts a confusion matrix 900 for this best performing model, which provides a visual indication of how well the diagnoses predicted by the model (905) line up with the actual diagnoses 910. The confusion matrix reveals two types of mistakes occasionally made by the machine learning model: predicting a cognitively normal diagnosis when a patient is actually diagnosed with MCI and predicting an MCI diagnosis when a patient is actually diagnosed with dementia. These mistakes may both simply be the result of a small error in how the time variable is applied by the algorithm, which creates a lag in the diagnosis predictions.

Figure 10:
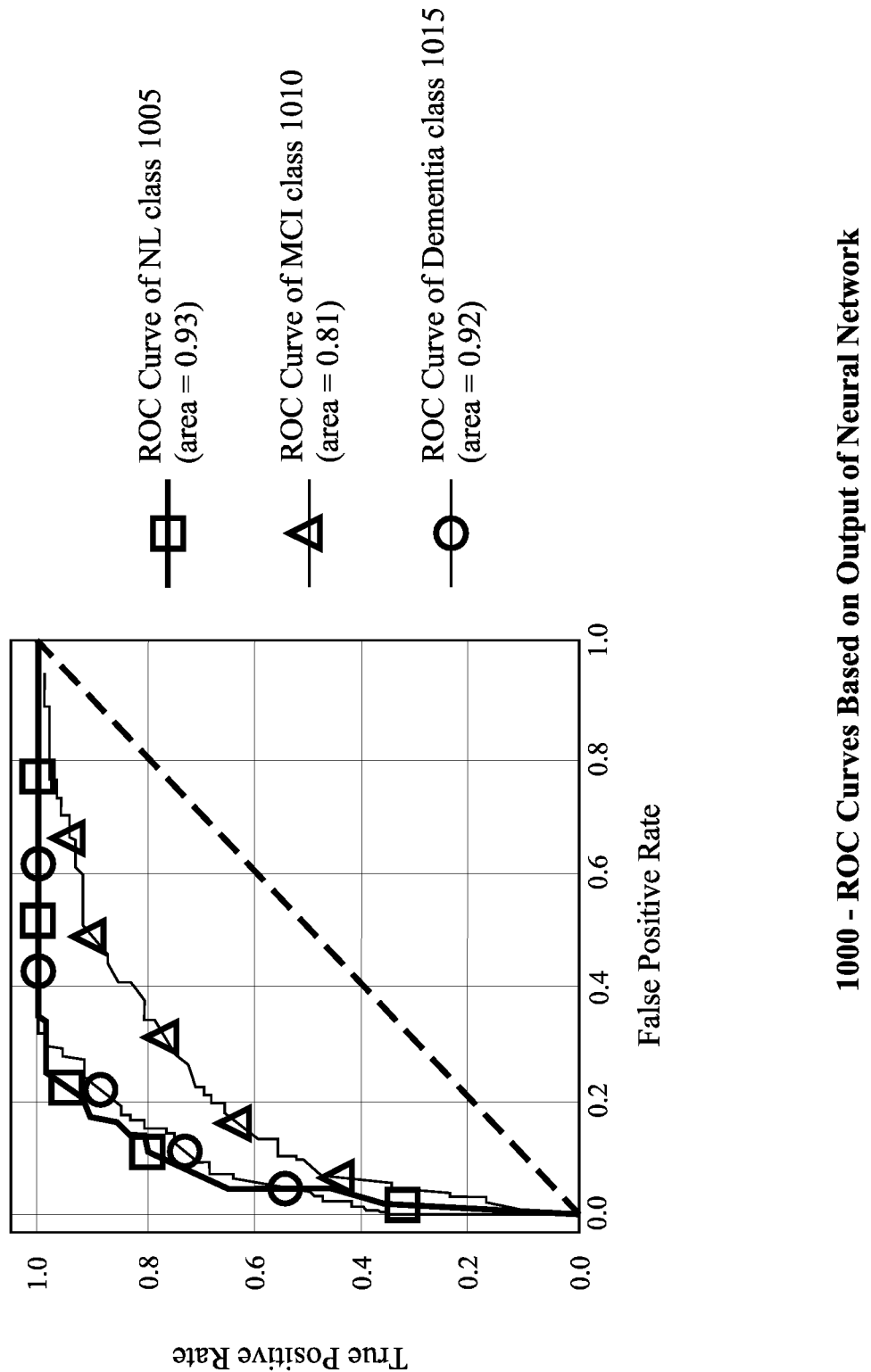
FIG. 10 illustrates an example Receiver Operating Characteristic (ROC) curve.

FIG. 10 shows a group of Receiver Operating Characteristic (ROC) curves 1000 based on the output of the best performing model, which measure how well the model can separate two groups: patients with a particular diagnosis and patients with one of the other diagnoses. Interestingly, the ROC score for the MCI class 1010 is lower than the other two ROC scores (NL class 1005 and Dementia class 1015), suggesting that the model is having more difficulty separating patients with MCI from the other two groups. Based on these individual ROC scores, the model's average mAUC score (0.866) could be dramatically increased if the model's ability to separate MCI patients from non-MCI patients was improved.

Figure 11:
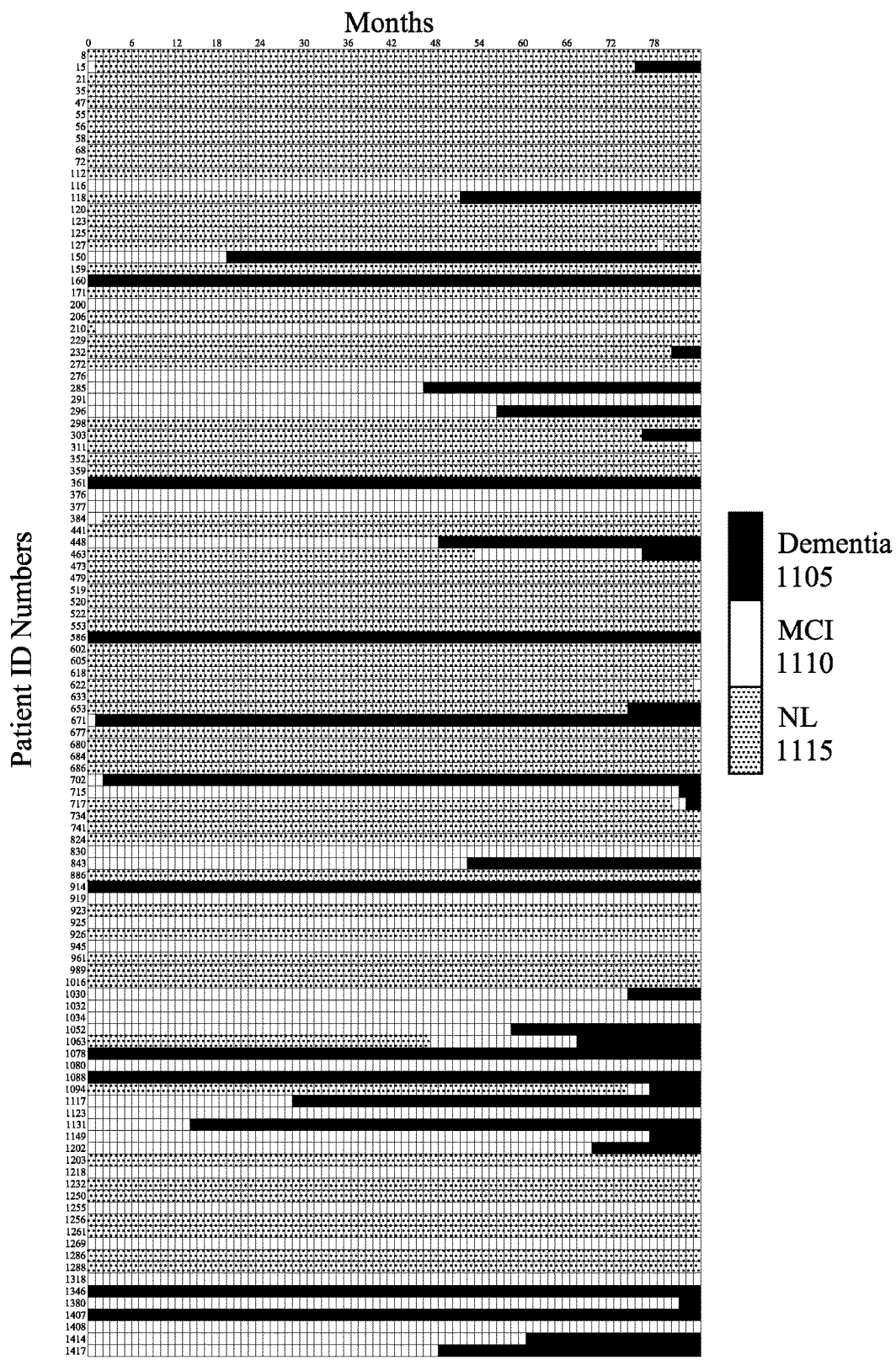
FIG. 11 illustrates an example graphical illustration of month-by-month predicted diagnoses.

The best performing model was also used to predict the future diagnosis of normal, MCI, or dementia for all 110 patients in the LB2/LB4 datasets on a month-to-month basis over an 84-month (7-year) period, as shown in chart 1100 of FIG. 11. The model predicted that some of the patients would remain normal ("NL" 1115) over the entire 7-year period, while others would progress from normal to MCI 1110 to dementia 1105.

Time courses may also be generated for these patients (e.g., a subset, such as n=50) showing how the likelihood of normal, MCI, or dementia diagnoses is forecast to vary over some time period (e.g., 84 months). As would be seen by the time courses, patients who remained normal over the entire 84-month period generally received very low predicted probabilities of MCI or dementia diagnoses from the model. Similarly, patients who were diagnosed with dementia at some point during this period generally received high predicted probabilities of dementia from the model.

CONCLUSION

Previous work published by others has shown that machine learning algorithms can accurately classify a patient's current cognitive state (normal, MCI, or dementia) using contemporaneous clinical data. The techniques herein have extended this previous work by looking at how past and present clinical data can be used to predict a patient's future cognitive state and by developing machine learning models that can correlate clinical data obtained from patients at one time point with the progression of Alzheimer's disease in the future. Several of the machine-learning models used herein are effective at predicting the progression of Alzheimer's disease, both in cognitively normal patients and patients suffering from MCI. Additionally, a novel All-Pairs technique was developed to compare all possible pairs of temporal data points for each patient to generate the training dataset. By comparing data points at different points in time, the All-Pairs technique adds time as a variable and therefore does not require fixed time intervals, which are unlikely to occur in "real-life" data. These techniques could be used to identify patients having high Alzheimer's disease risk before they are diagnosed with MCI or dementia and who would therefore make good candidates for clinical trials for Alzheimer's disease therapeutics. Since the inability to identify Alzheimer's disease patients at early stages is believed to be one of the primary reasons for the frequent failure of Alzheimer's disease clinical trials, these techniques may help increase the chances of finding a treatment for Alzheimer's disease.

While there have been shown and described illustrative embodiments that provide for machine-learning-based detection of Alzheimer's disease, it is to be understood that various other adaptations and modifications may be made within the spirit and scope of the embodiments herein. For example, while certain embodiments are described herein with respect to using certain models for purposes of machine-learning-based detection, the models are not limited as such and may be used for other functions, in other embodiments. For example, the techniques described herein may be used to identify patients having high Alzheimer's disease risk before they are diagnosed with MCI or dementia and who would therefore make good candidates for clinical trials for Alzheimer's disease therapeutics. In addition, while certain biomarkers are shown, other suitable biomarkers may be used, accordingly. For instance, other suitable biomarkers may include, but are not limited to, T-tau, P-tau 181, and Abeta 1-42, as well as various measurements based on images obtained by MRI, positron emission tomography, or other medical imaging techniques.

Illustratively, the techniques described herein may be performed by hardware, software, and/or firmware, such as in accordance with a machine learning process, which may include computer executable instructions executed by a processor or plurality of processors to perform functions relating to the techniques described herein, e.g., within a single computing device or else through coordination between a plurality of computing devices across a computer network.

Figure 12:
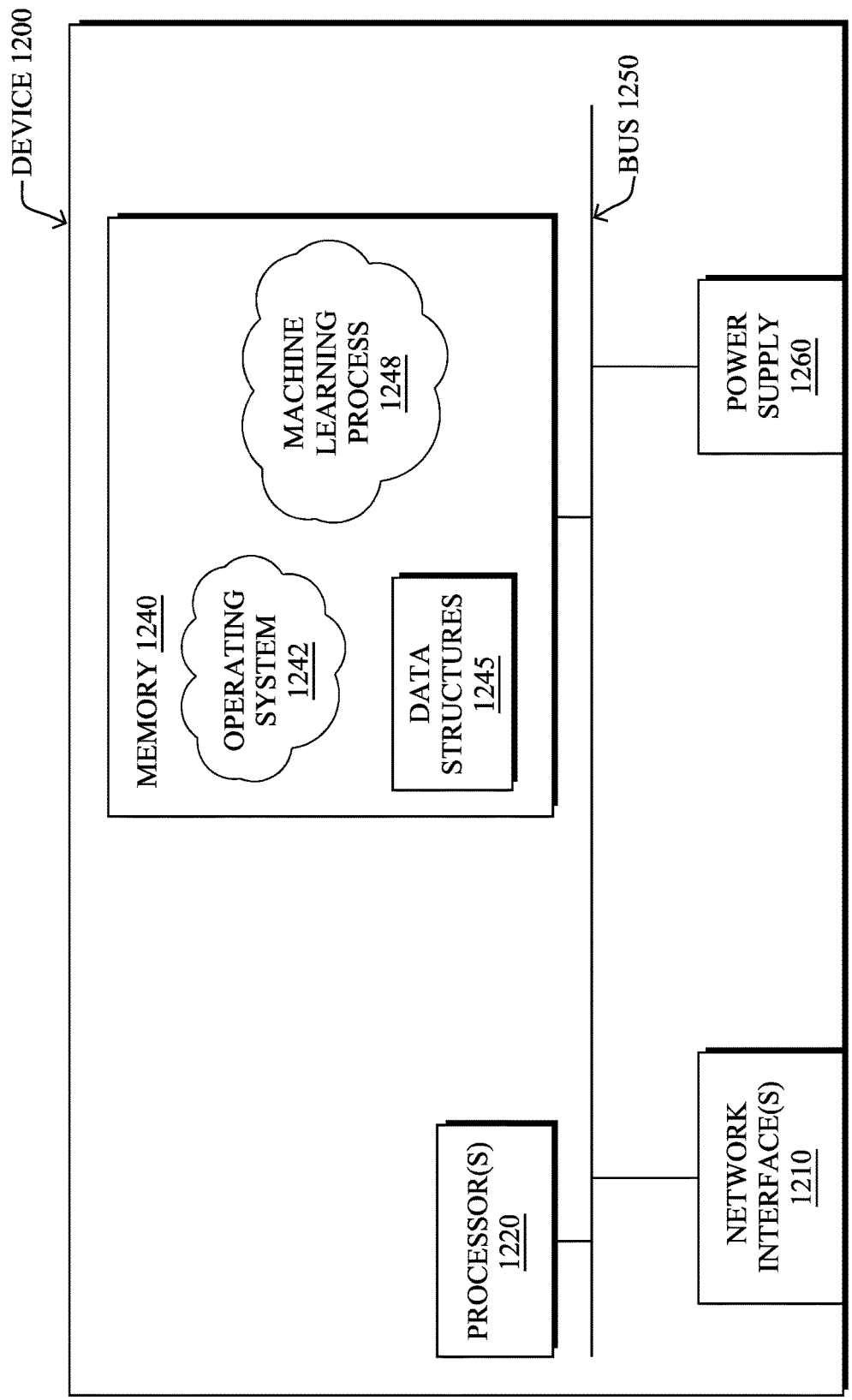
FIG. 12 illustrates an example simplified machine learning computing device.

FIG. 12 is a schematic block diagram of an example computing device 1200 that may be used with one or more embodiments described herein, e.g., as a server, personal computer, cloud computing process, datacenter, and any other computing device that supports the operations of the techniques herein. Device 1200 comprises one or more network interfaces 1210, one or more processors 1220, and a memory 1240 interconnected by a system bus 1250, and is powered by a power supply 1260.

The network interfaces 1210 include the mechanical, electrical, and signaling circuitry for communicating data over physical or wireless links coupled to a computer network (e.g., for receiving the training data, as mentioned above). The network interfaces may be configured to transmit and/or receive data using a variety of different communication protocols.

The memory 1240 comprises a plurality of storage locations that are addressable by the processor(s) 1220 for storing software programs and data structures associated with the embodiments described herein. The processor 1220 may comprise necessary elements or logic adapted to execute the software programs and manipulate the data structures 1245. An operating system 1242, portions of which are typically resident in memory 1240 and executed by the processor(s), functionally organizes the device by, among other things, invoking operations in support of software processes and/or services executing on the device. These software processes and/or services may comprise an illustrative machine learning process 1248, configured to perform one or more aspects of the techniques as described in detail above when executed by the processor(s) 1220.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, while processes may be shown and/or described separately, those skilled in the art will appreciate that processes may be routines or modules within other processes.

Figure 13:
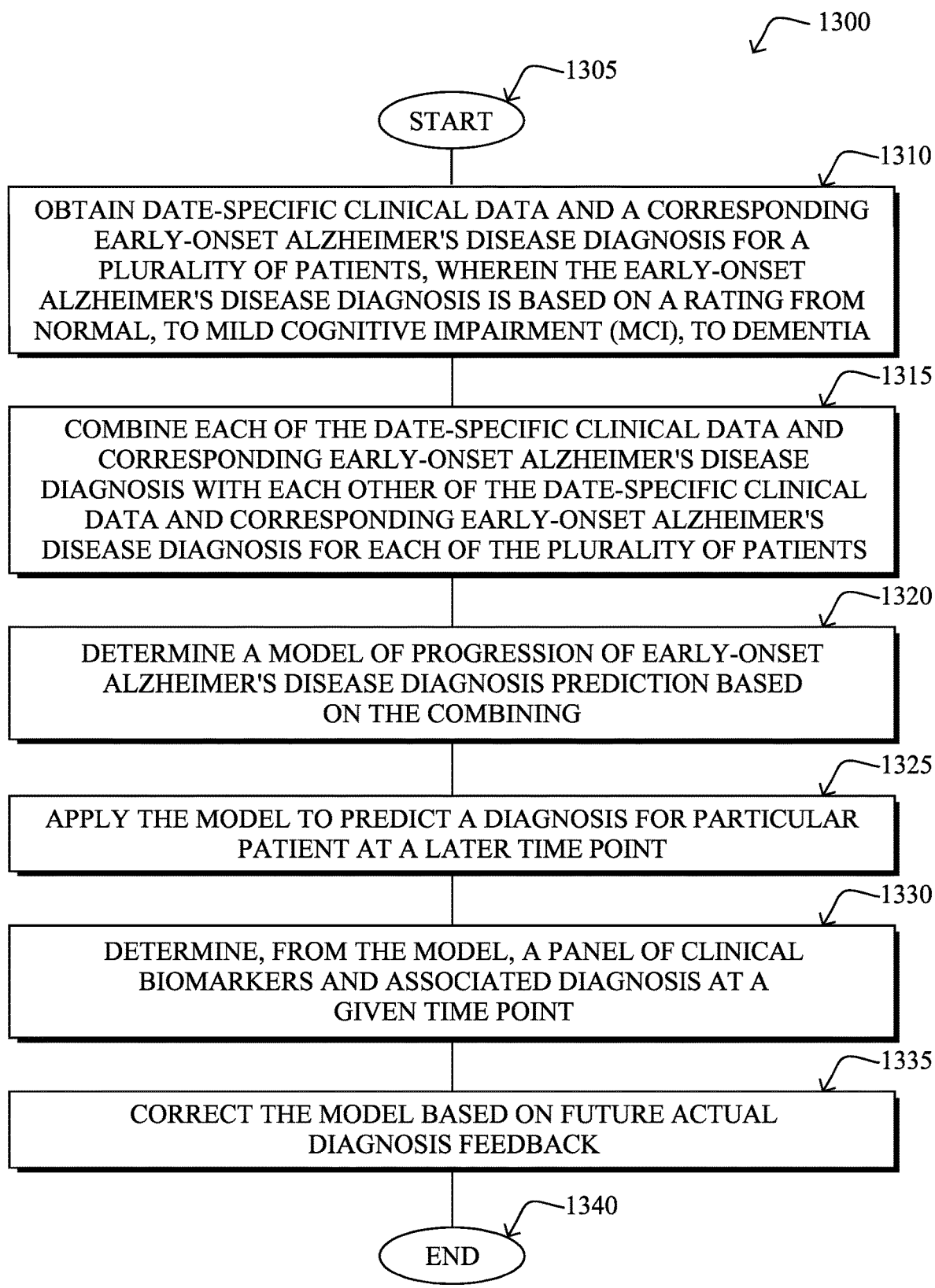
FIG. 13 illustrates another example simplified procedure for machine-learning-based forecasting of the progression of Alzheimer's disease.

In addition, FIG. 13 illustrates another example procedure 1300 according to the techniques herein (e.g., performed by machine learning process 1248), specifically relating to the all-pairs technique. The procedure may start at step 1305, and continues to step 1310 where, as described above, a machine learning process obtains date-specific clinical data and a corresponding diagnosis for a plurality of patients, wherein the diagnosis is based on a rating from normal, to mild cognitive impairment (MCI), to dementia. Note that as described above, obtaining date-specific clinical data and corresponding diagnosis for the plurality of patients may be based on an Alzheimer's Disease Neuroimaging Initiative (ADNI) database.

In step 1315, the machine learning process combines each of the date-specific clinical data and corresponding diagnosis with each other of the date-specific clinical data and corresponding diagnosis for each of the plurality of patients (e.g., combining pairs of data or combining triplets of data). Note that the machine learning process may be based on a multilayer perceptron (MLP) classifier or recurrent neural network (RNN) classifier, as described above.

In step 1320, the machine learning process may then determine a model of progression of diagnosis prediction based on the combining. Note that the model may be based on a time interval between timepoints of the date-specific data, as described above.

In addition, in certain embodiments, in step 1325, the model may be applied to predict a diagnosis for particular patient at a later time point. Also, in step 1330, the model may be used to determine a panel of clinical biomarkers and associated diagnosis at a given timepoint. In still another optional embodiment, in step 1335, the model may be corrected based on future actual diagnosis feedback.

The simplified procedure 1300 may then end in step 1340. Notably, the steps shown above are one illustrative embodiment, and are not meant to be limiting to the scope of the embodiments herein. Additional or fewer steps may be used, and the order of the steps may be changed in certain instances.

The foregoing description has been directed to specific embodiments. It will be apparent, however, that other variations and modifications may be made to the described embodiments, with the attainment of some or all of their advantages. For instance, it is expressly contemplated that certain components and/or elements described herein can be implemented as software being stored on a tangible (non-transitory) computer-readable medium (e.g., disks/CDs/RAM/EEPROM/etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method, comprising:
   obtaining, by a device, date-specific clinical data and a corresponding diagnosis for a plurality of patients, wherein the diagnosis is based on a rating from normal, to mild cognitive impairment (MCI), to dementia;
   combining, by the device, each of the date-specific clinical data and corresponding diagnosis with each other of the date-specific clinical data and corresponding diagnosis for each of the plurality of patients;
   generating, by the device, a feature array and a target array based on the combined date-specific clinical data and corresponding diagnoses, wherein the feature array comprises data indicative of one or more biomarkers of a particular patient at a first examination and a clinical state of the particular patient at the first examination, the one or more biomarkers including one or more copies of the ε4 allele of the APOE gene, and wherein the target array comprises data indicative of a clinical state of the particular patient at a second examination later than the first examination;
   training, by the device, a machine learning model to predict a future diagnosis for the particular patient using the generated feature array and target array; and
   applying, by the device, the trained machine learning model to predict a future diagnosis for the particular patient.

2. The method as in claim 1, wherein combining comprises:
   combining pairs of data.

3. The method as in claim 1, wherein combining comprises:
   combining triplets of data.

4. The method as in claim 1, further comprising:
   determining, from the machine learning model, a panel of clinical biomarkers and associated diagnosis at a given timepoint.

5. The method as in claim 1, wherein the machine learning model is based on a time interval between timepoints of the date-specific data.

6. The method as in claim 1, wherein the machine learning model is based on a multilayer perceptron (MLP) classifier.

7. The method as in claim 1, wherein the machine learning model is based on a recurrent neural network (RNN) classifier.

8. The method as in claim 1, wherein obtaining date-specific clinical data and corresponding diagnosis for the plurality of patients is based on an Alzheimer's Disease Neuroimaging Initiative (ADNI) database.

9. The method as in claim 1, further comprising:
   correcting the machine learning model based on future actual diagnosis feedback.

10. A tangible, non-transitory computer-readable media comprising instructions executable by a processor for executing a process comprising:
    obtaining date-specific clinical data and a corresponding diagnosis for a plurality of patients, wherein the diagnosis is based on a rating from normal, to mild cognitive impairment (MCI), to dementia;
    combining each of the date-specific clinical data and corresponding diagnosis with each other of the date-specific clinical data and corresponding diagnosis for each of the plurality of patients;
    generating a feature array and a target array based on the combined date-specific clinical data and corresponding diagnoses, wherein the feature array comprises data indicative of one or more biomarkers of a particular patient at a first examination and a clinical state of the particular patient at the first examination, the one or more biomarkers including one or more copies of the ε4 allele of the APOE gene, and wherein the target array comprises data indicative of a clinical state of the particular patient at a second examination later than the first examination;

training a machine learning model to predict a future diagnosis for the particular patient using the generated feature array and target array; and applying the trained machine learning model to predict a future diagnosis for the particular patient.

11. The computer-readable medium as in claim 10, wherein combining comprises:
combining pairs of data.

12. The computer-readable medium as in claim 10, wherein combining comprises:
combining triplets of data.

13. The computer-readable medium as in claim 10, wherein the process further comprises:
applying the machine learning model to predict a diagnosis for particular patient at a later time point.

14. The computer-readable medium as in claim 10, wherein the process further comprises:
determining, from the machine learning model, a panel of clinical biomarkers and associated diagnosis at a given timepoint.

15. The computer-readable medium as in claim 10, wherein the machine learning model is based on a time interval between timepoints of the date-specific data.

16. The computer-readable medium as in claim 10, wherein the machine learning model is based on a multilayer perceptron (MLP) classifier.

17. The computer-readable medium as in claim 10, wherein the machine learning model is based on a recurrent neural network (RNN) classifier.

18. The computer-readable medium as in claim 10, wherein obtaining date-specific clinical data and corresponding diagnosis for the plurality of patients is based on an Alzheimer's Disease Neuroimaging Initiative (ADNI) database.

19. The computer-readable medium as in claim 10, wherein the process further comprises:
correcting the machine learning model based on future actual diagnosis feedback.

* * * * *